United States Patent
Akiyama et al.

(10) Patent No.: US 11,746,315 B2
(45) Date of Patent: Sep. 5, 2023

(54) BIOLOGICAL TISSUE FABRICATION INFORMATION GENERATING DEVICE, BIOLOGICAL TISSUE FABRICATION SYSTEM, AND MEDICAL EXPENSE CALCULATION SYSTEM

(71) Applicant: KANEKA CORPORATION, Osaka (JP)

(72) Inventors: Hirokazu Akiyama, Kobe (JP); Masaki Ichimura, Kobe (JP); Hirotoshi Matsuta, Kobe (JP)

(73) Assignee: KANEKA CORPORATION, Osaka (JP)

( * ) Notice: Subject to any disclaimer, the term of this patent is extended or adjusted under 35 U.S.C. 154(b) by 1441 days.

(21) Appl. No.: 15/764,203

(22) PCT Filed: Sep. 5, 2016

(86) PCT No.: PCT/JP2016/076034
§ 371 (c)(1),
(2) Date: Mar. 28, 2018

(87) PCT Pub. No.: WO2017/056866
PCT Pub. Date: Apr. 6, 2017

(65) Prior Publication Data
US 2018/0273886 A1 Sep. 27, 2018

(30) Foreign Application Priority Data
Sep. 29, 2015 (JP) ................. 2015-192077

(51) Int. Cl.
*C12M 3/00* (2006.01)
*C12M 1/26* (2006.01)
*G16H 50/50* (2018.01)
*C12N 5/071* (2010.01)
*G16H 40/63* (2018.01)
*G16H 40/20* (2018.01)
*G06Q 10/10* (2023.01)
*B33Y 50/00* (2015.01)
*G16H 50/20* (2018.01)
*C12M 1/12* (2006.01)
*C12M 1/34* (2006.01)
*C12M 1/36* (2006.01)
*C12N 5/00* (2006.01)
*G06Q 30/04* (2012.01)

(52) U.S. Cl.
CPC ............. *C12M 21/08* (2013.01); *B33Y 50/00* (2014.12); *C12M 25/00* (2013.01); *C12M 33/00* (2013.01); *C12M 41/46* (2013.01); *C12M 41/48* (2013.01); *C12N 5/0062* (2013.01); *C12N 5/0697* (2013.01); *G06Q 10/10* (2013.01); *G06Q 30/04* (2013.01); *G16H 40/20* (2018.01); *G16H 40/63* (2018.01); *G16H 50/20* (2018.01); *G16H 50/50* (2018.01); *C12N 2513/00* (2013.01)

(58) Field of Classification Search
None
See application file for complete search history.

(56) References Cited

U.S. PATENT DOCUMENTS

| 2007/0083286 A1 | 4/2007 | Kobayashi |
| 2011/0129892 A1 | 6/2011 | Umezu et al. |
| 2014/0120192 A1 | 5/2014 | Nakayama et al. |
| 2015/0105891 A1 | 4/2015 | Golway et al. |

FOREIGN PATENT DOCUMENTS

| JP | 2002-236744 A | 8/2002 |
| JP | 2003-263495 A | 9/2003 |
| JP | 2003-281270 A | 10/2003 |
| JP | 2005-080599 A | 3/2005 |
| JP | 2005-224106 A | 8/2005 |
| JP | 2005-258720 A | 9/2005 |
| JP | 2013-005751 A | 1/2013 |
| WO | WO 2007/074500 A1 | 7/2007 |
| WO | WO 2010/008002 A1 | 1/2010 |

OTHER PUBLICATIONS

Sun and Darling et al. (Biotechnol. Appl. Biochem. (2004) vol. 39:29-47). (Year: 2004).*
English language translation of the Written Opinion of the International Searching Authority issued in corresponding International Application No. PCT/JP2016/076034 dated Nov. 22, 2016.
International Search Report (PCT/ISA/210) issued in PCT/JP2016/076034, dated Nov. 22, 2016.
Nakamura, Makoto, "Kogaku ni yoru Soshiki Sakusei Bioprinting & Biofabrication", Dai 10 Kai Dobutsusei Shugohai no Toriatsukai ni Kansuru Sagyobukai, Jun. 10, 2015, pp. 1-57.

(Continued)

Primary Examiner — Lori A. Clow
(74) Attorney, Agent, or Firm — Birch, Stewart, Kolasch & Birch, LLP

(57) ABSTRACT

[PROBLEM] It is an object to provide a biological tissue fabrication information generating device that generates biological tissue fabrication information for fabrication of tissue imitative of the structure of the biological tissue of a patient, a biological tissue fabrication system that fabricates biological tissue based on biological tissue fabrication information, and a medical expense calculation system that calculates the medical expense of a patient receiving therapeutic graft of biological tissue.

[SOLUTION MEANS] A biological tissue fabrication information generating device characterized in that it comprises structure information storage unit 10 that stores tissue structure information D1 indicating three-dimensional structure of biological tissue of patient Pt, and biological tissue fabrication information generator 11 that generates biological tissue fabrication information D3 in the form of information linking respective locations within biological tissue indicated by tissue structure information D1, and the types of cells that should be arranged at such respective locations, based on tissue structure information D1 and cell type information D4 for determining types of cells at respective locations in biological tissue indicated by tissue structure information D1.

2 Claims, 10 Drawing Sheets

(56) References Cited

OTHER PUBLICATIONS

Saito et al., "3D Printing Technology of Tissues and Organs Using the 3D Gel Printer", Cell Technology, vol. 34, No. 2, 2015, pp. 184-189.
Takato et al., "Reconstruction of maxillofacial region using bone and cartilage regenerative medicine", Regenerative Medicine, vol. 14, No. 3, 2015, pp. 46-51.
Yamamoto et al., "Bateijin no 3D Kekkan Imaging to 3D Printer o Mochiita Zoki Zokei-Bateijin ni Tomonatta Sakakyoku Jin Saibo Gan Shujutsu-", Nephrology Frontier, vol. 14, No. 3, 2015, pp. 56-60.
Palacek, "Plunpoten Stem Cells: Sources and Characterization", Tissue Engineering From Lab to Clinic, Springer Science & Business Media, Jan. 1, 2011, XP055666481, pp. 79 (1 page).
Sun et al., "Bio-CAD Modeling and its Applications in Computer-aided Tissue Engineering", Computer-Aided Design, vol. 37, No. 11, Sep. 1, 2005, pp. 1097-1114.
Li et al., "Progresses of Induced Pluripotent Stem Cells in Oral Tissue Engineering," Journal of Dental Prevention and Treatment, Mar. 31, 2014, pp. 162-165 (total 6 pages), with a partial English translation.

\* cited by examiner (a)

| Substitute cell type information D6 | |
|---|---|
| Type of cells intended to be arranged | Cells capable of being substituted therefor |
| Vascular endothelial cells | iPS cells, ES cells, vascular endothelial precursor cells |
| Myocardial cells | iPS cells, ES cells |
| Nerve cells | iPS cells, ES cells, neural stem cells |
| Osteoblasts | iPS cells, ES cells, mesenchymal stem cells |
| A cells | iPS cells, ES cells, X cells |
| B cells | iPS cells, ES cells, Y cells |

BIOLOGICAL TISSUE FABRICATION INFORMATION GENERATING DEVICE, BIOLOGICAL TISSUE FABRICATION SYSTEM, AND MEDICAL EXPENSE CALCULATION SYSTEM

TECHNICAL FIELD

The present invention relates to a biological tissue fabrication information generating device that generates biological tissue fabrication information for fabrication of a biological tissue imitative of the structure of the biological tissue of a patient, to a biological tissue fabrication system that fabricates biological tissue based on biological tissue fabrication information, and to a medical expense calculation system for calculating the medical expense of a patient receiving a therapeutic graft of the biological tissue.

BACKGROUND ART

Regenerative medicine, in which treatment is carried out by regenerating cells, has received attention in recent years as a new type of treatment for injuries and diseases not treatable by conventional means.

Therefore, development of techniques that will lead to advancement of regenerative medicine technology has been sought. More particularly, technologies related to tissue engineering, in which cells and support structure (scaffold) are combined to fabricate tissues having three-dimensional structure, have come to hold an important place in the advancement of regenerative medicine.

In conventional art, to fabricate biological tissue having three-dimensional structure, for example, cells are subsequently seeded on support structures comprising polylactic acid, polyglycolic acid. But because it is not possible to control the arrangement of cells within tissue, it has been difficult to fabricate complex tissue in which a plurality of types of cells are systematically arranged in sophisticated fashion as is the case in actual biological tissue. On the other hand, to solve this problem, new technologies that enable to fabricate tissues by precisely arranging multiple types of cells at desired locations in a three-dimensional fashion have been recently developed. For example, Patent Reference No. 1 discloses an apparatus that utilizes the electrostatic inkjet phenomenon to carry out patterning of cells and extracellular matrix, and Patent Reference No. 2 discloses an apparatus that causes clusters of cells to be impaled on needle-like bodies.

Furthermore, because actual biological tissue is made up of a great many types of cells (cellular varieties), procurement of each of the various types of cells is an important problem for fabrication of biological tissue having a cellular type composition which is similar to that of biological tissue. Methods, in which target cells are prepared by causing differentiation to be induced in pluripotent stem cells such as embryonic stem cells (ES cells), or induced in pluripotent stem cells (iPS cells) and somatic stem cells such as mesenchymal stem cells (MSC), are conventionally favored approaches. Marked technological advances having been made with such methods, the problems associated with procurement of cells required for tissue fabrication have been solved.

Moreover, for the advancement of regenerative medicine, besides technology for fabrication of tissue having three-dimensional structure, it is also necessary to develop systems to fabricate and provide tissue appropriate for a patient in correspondence to disease and/or injury condition of the patient. For example, Patent Reference No. 3 discloses a method for providing medical substance information that is capable of causing an image of a defective location and/or a diseased location within the body of a patient to be transmitted, and of causing the quantity of cultured skin tissue(s) required for treatment to be provided to a medical institution based on that image.

PRIOR ART REFERENCES

Patent References

PATENT REFERENCE NO. 1: WO2010/008002A1
PATENT REFERENCE NO. 2: Japanese Patent Application Publication Kokai No. 2013-5751
PATENT REFERENCE NO. 3: Japanese Patent Application Publication Kokai No. 2003-281270

SUMMARY OF INVENTION

Problem to be Solved by Invention

However, the method disclosed at Patent Reference No. 3 is specialized for structurally simple tissue such as that of the skin or cornea which does not require any consideration of differences in tissue structure which vary depending on patient. For this reason, it has been difficult to apply this method to regenerative medicine for complex biological tissue comprising a variety of types of cells that are systematically arranged in sophisticated fashion. This being the case, development of a system and/or device, which make it possible to fabricate tissue that requires consideration of differences in tissue structure which vary depending on patient, has been sought for. And with regard to the devices disclosed at Patent Reference No. 1 and Patent Reference No. 2, because these fabricate tissue based on information that has been entered into the device in advance, it has been difficult with them to fabricate tissue imitative of biological tissue that varies from patient to patient.

The present invention was conceived in light of such problems, it being an object thereof to provide a biological tissue fabrication information generating device that generates biological tissue fabrication information for fabrication of biological tissue imitative of the structure of the biological tissue of a patient, a biological tissue fabrication system that fabricates biological tissue based on biological tissue fabrication information, and a medical expense calculation system that calculates the medical expense of a patient receiving therapeutic graft of biological tissue.

Means for Solving Problem

A biological tissue fabrication information generating device in accordance with one aspect of the present invention generates biological tissue fabrication information for fabrication of biological tissue of a patient by generating cells, the biological tissue fabrication information generating device which comprises a structure information storage unit that stores tissue structure information indicating a three-dimensional structure of the biological tissue of the patient; and a biological tissue fabrication information generator that, based on the tissue structure information and cell type information for determining cell types at respective locations in the biological tissue indicated by the tissue structure information, generates the biological tissue fabrication information in the form of information linking to the respective locations within the biological tissue indicated by said tissue structure information, and types of cells to be arranged at those respective locations.

In accordance with such constitution, because the biological tissue fabrication information generating device generates biological tissue fabrication information, it is possible to obtain information required for fabrication of biological tissue of three-dimensional structure.

Furthermore, in accordance with such constitution, because the biological tissue fabrication information is information linking to respective locations within the biological tissue and types of cells that should be arranged at those respective locations based on information pertaining to the three-dimensional structure of the biological tissue of the patient, the biological tissue fabrication information generating device in accordance with the aspect of the present invention is able to generate information which makes it possible to precisely fabricate the structure of biological tissue of the patient that comprises cells of a plurality of types that are systematically arranged in sophisticated fashion.

Furthermore, this may further comprise a cell type information storage unit wherein the cell type information is stored in advance; wherein the cell type information is information indicating correspondence between the respective locations within the biological tissue and the cell types.

In accordance with such constitution, because cell types corresponding to respective locations within biological tissue are stored in advance at the cell type information storage unit separately for each type of biological tissue, it is possible to specify types of cells constituting respective locations.

Furthermore, this apparatus may further comprise a cell type information generator that generates the cell type information from the tissue structure information; wherein the tissue structure information includes information permitting identification of the cell types at the respective locations within the biological tissue.

In accordance with such constitution, because it is possible to identify types of cells at respective locations within the biological tissue of the patient from tissue structure information obtained as a result of clinical testing, it is possible to generate biological tissue fabrication information that accurately reflects the respective types of cells in the biological tissue of the patient and the locations thereof.

Furthermore, there may be a variety of types of the cells; the biological tissue fabrication information generating device may further comprise a substitute cell storage unit, which stores in advance substitute cell type information linking to substitute cell types capable of being substituted for at least some types of cells among the plurality of the types of the cells with types of cells for which the substitute cell types may be substituted; and, at the biological tissue fabrication information, the biological tissue fabrication information generator may cause the substitute cell types to be linked to and employed as the cell types to be arranged at the respective locations based on the substitute cell type information.

In accordance with such constitution, because substitute cell type information linking to cell types capable of being substituted for cells originally intended to be arranged thereat is stored at the substitute cell storage unit, it is possible to generate biological tissue fabrication information such as will permit other types of cells to be used to fabricate the target biological tissue.

Furthermore, this apparatus may further comprise a support structure information storage unit, which stores in advance support structure information linking to types of the biological tissue with types of support structures appropriate for fabrication of said biological tissue; and a support structure selector that selects a support structure based on type of the biological tissue; wherein the biological tissue fabrication information generator generates the biological tissue fabrication information in such fashion as to cause the support structure selected by the support structure selector to be employed for fabrication of the biological tissue.

In accordance with such constitution, because support structure information linking to types of biological tissue and types of support structures appropriate for fabrication of said biological tissue is stored in advance at the support structure information storage unit, it is possible, based on said information for the support structure selector, to select support structures appropriate for the biological tissue to be fabricated.

Furthermore, this apparatus may further comprise a structure difference calculator that, based on the tissue structure information for the patient and tissue structure information which is an earlier version thereof than that tissue structure information for that patient, determines a difference between a structure indicated by the tissue structure information and a structure indicated by the earlier version of the tissue structure information; wherein the biological tissue fabrication information generator generates the biological tissue fabrication information based on a difference determined by the structure difference calculator.

In accordance with such constitution, because the structure difference calculator, based on tissue structure information for a patient and tissue structure information which is an earlier version thereof than that tissue structure information for that patient, determines a difference between a structure indicated by the tissue structure information and a structure indicated by the earlier version of the tissue structure information, it is possible to generate biological tissue fabrication information such as will permit fabrication of biological tissue at regions where there are structural differences.

Furthermore, this apparatus may further comprise a cell number calculator that calculates a number of cells required for fabrication of the biological tissue based on the biological tissue fabrication information generated by the biological tissue fabrication information generator.

In accordance with such constitution, because the cell number calculator calculates the number of cells required for fabrication of the target biological tissue based on the biological tissue fabrication information, it is possible to obtain the number of cells required for fabrication of biological tissue.

Furthermore, this may further comprise a cell preparation expense information storage unit, which stores cell preparation expense information linking to a number of cells and information pertaining to an expense of preparing that number of cells; and a fabrication expense calculator that, based on the cell preparation expense information and the number of cells required for fabrication of the biological tissue calculated by the cell number calculator, calculates biological tissue fabrication expense information for fabrication of the biological tissue.

In accordance with such constitution, because the cell preparation expense information storage unit stores cell preparation expense information linking to the number of cells and information pertaining to the expense of preparing that number of cells, and because the fabrication expense calculator, based on this cell preparation expense information and the number of cells required for fabrication of the biological tissue, calculates biological tissue fabrication expense information for fabrication of the biological tissue, it is possible to obtain the expense required for fabrication of the biological tissue.

Moreover, a biological tissue fabrication system in accordance with one aspect of the present invention has the biological tissue fabrication information generating device; and a cell three-dimensional arrangement fabrication device comprising a cell three-dimensional arrangement unit that fabricates the biological tissue by causing cells to be three-dimensionally arranged based on the biological tissue fabrication information generated by the biological tissue fabrication information generating device.

In accordance with such constitution, because the biological tissue fabrication information generating device generates biological tissue fabrication information linking to respective locations within the biological tissue and types of cells that should be arranged at those respective locations, and because the cell three-dimensional arrangement fabrication device fabricates biological tissue by causing cells to be three-dimensionally arranged based on said biological tissue fabrication information, the biological tissue fabrication system in accordance with the aspect of the present invention is able to precisely fabricate biological tissue imitative of the structure of the actual biological tissue of a patient which comprises cells of a plurality of types that are systematically arranged in sophisticated fashion.

Furthermore, the biological tissue fabrication system in accordance with the aspect of the present invention may further comprise a culture apparatus comprising a culture conditions determining unit that determines culture conditions for achieving a number of cells required for fabrication of the biological tissue by cells of the respective types based on the biological tissue fabrication information.

In accordance with such constitution, because the culture conditions determining unit determines, based on the biological tissue fabrication information, suitable culture conditions under which sufficient number of each of respective type cells to fabricate biological tissue can be generated, the culture apparatus is capable of preparing cells under optimal culture conditions.

A medical expense calculation system in accordance with one aspect of the present invention is for calculating a medical expense of a patient receiving therapeutic graft of biological tissue, the medical expense calculation system having the biological tissue fabrication information generating device and a treatment expense calculation device comprising a treatment expense calculator that calculates a treatment expense required for graft of said biological tissue, and being for calculating the medical expense of the patient receiving the therapeutic graft of the biological tissue based on biological tissue fabrication expense information generated by said biological tissue fabrication information generating device and treatment expense information generated by said treatment expense calculation device.

In accordance with such constitution, the medical expense of a patient receiving therapeutic graft of biological tissue can be calculated based on biological tissue fabrication expense information generated by a biological tissue fabrication information generating device and treatment expense information generated by a treatment expense calculation device.

Benefit of Invention

As described above, a biological tissue fabrication information generating device in accordance with one aspect of the present invention is able to generate biological tissue fabrication information for fabrication of biological tissue imitative of the structure of the biological tissue of a patient, a biological tissue fabrication system in accordance with one aspect of the present invention is able to fabricate biological tissue based on biological tissue fabrication information, and a medical expense calculation system in accordance with one aspect of the present invention is able to calculate the medical expense of a patient receiving therapeutic graft of biological tissue.

BRIEF DESCRIPTION OF DRAWINGS

FIG. 5($b$) is a three-dimensional image of a kidney indicated by the most recent healthy version of tissue structure information prior to partial nephrectomy; and FIG. 5($c$) is a three-dimensional image of a kidney indicated by structure difference information.

FIG. 10 Explanatory diagram showing an example of substitute cell type information.

EMBODIMENTS FOR CARRYING OUT INVENTION

Figure 1:
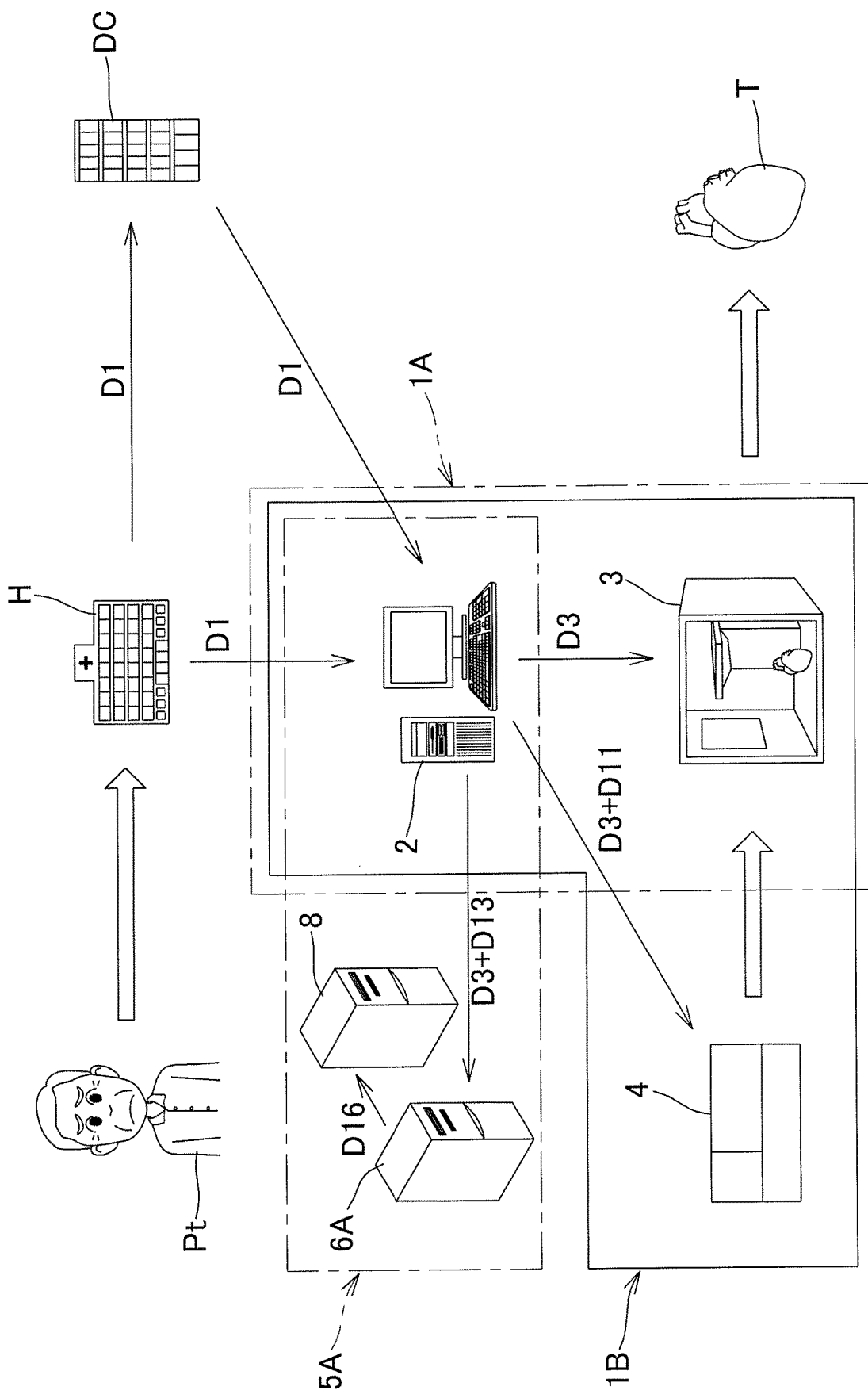
FIG. 1 Drawing for explaining a biological tissue fabrication information generating device, a biological tissue fabrication system, and a medical expense calculation system associated with embodiments of the present invention.
Figure 2:
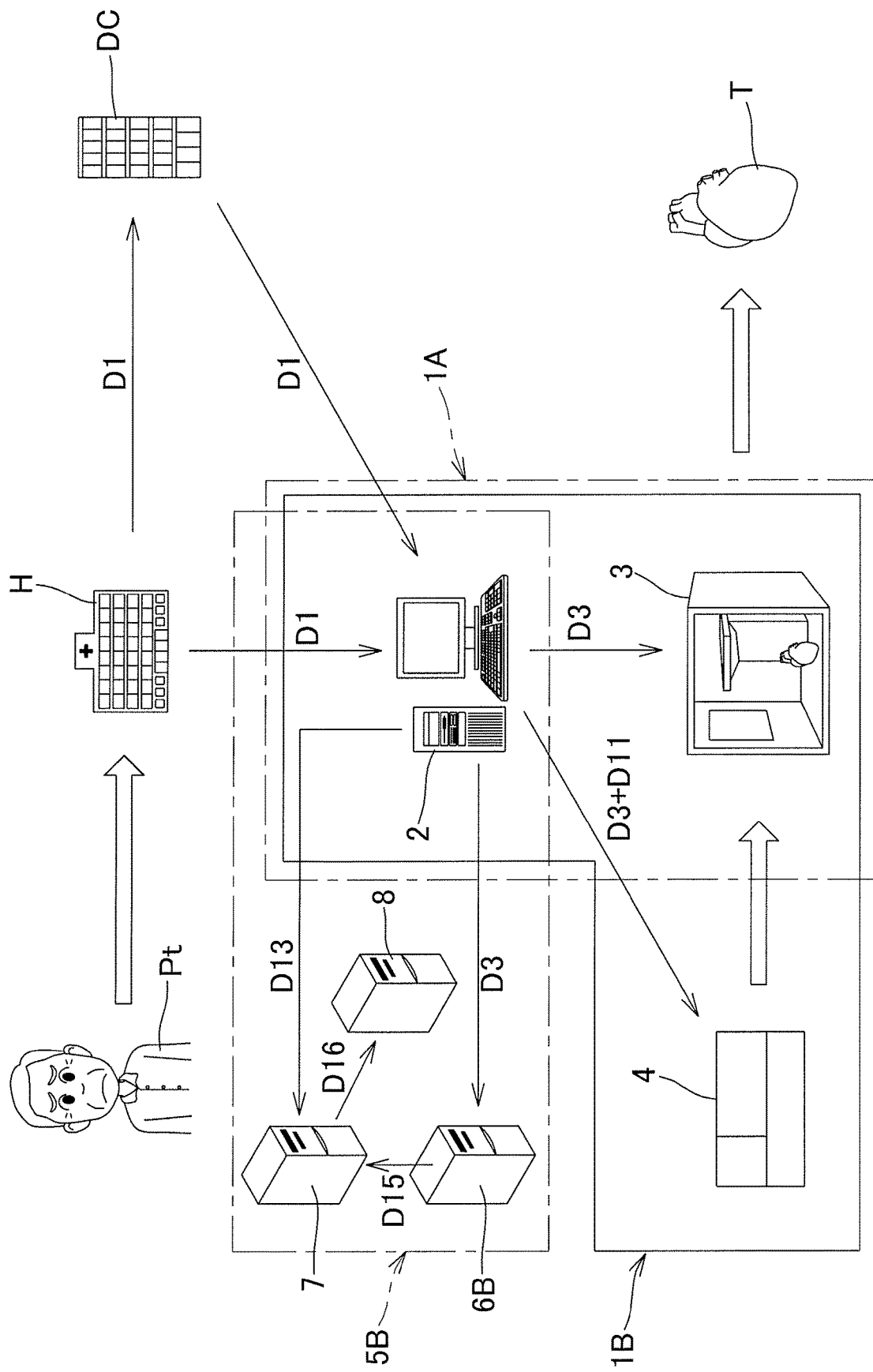
FIG. 2 Drawing for explaining a biological tissue fabrication information generating device, a biological tissue fabrication system, and a medical expense calculation system associated with embodiments of the present invention.
Figure 3:
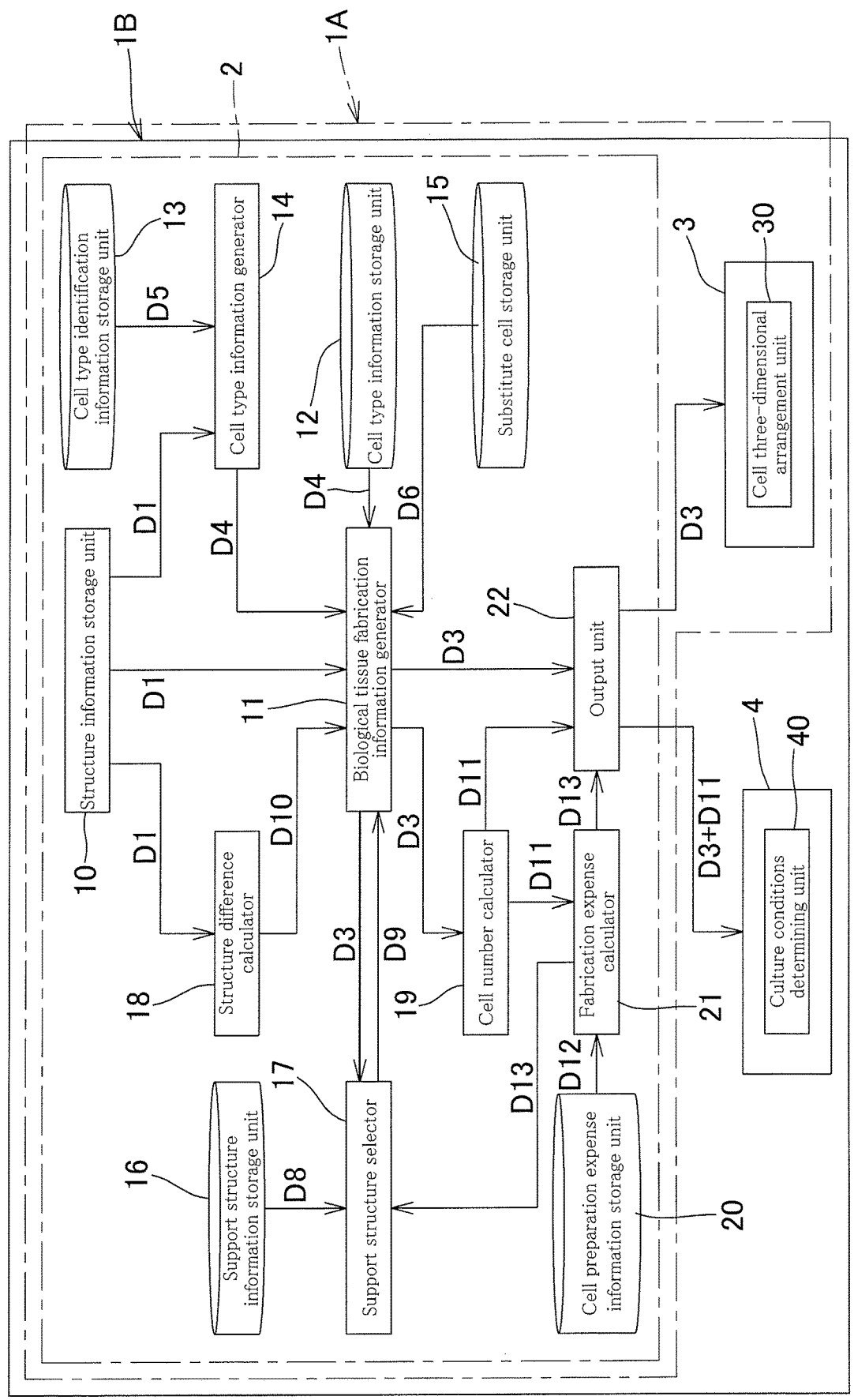
FIG. 3 Block diagram showing exemplary constitution of a biological tissue fabrication system and the biological tissue fabrication information generating device shown in FIG. 1 and FIG. 2.

As shown in FIG. 1, FIG. 2, and FIG. 3, biological tissue fabrication system 1A in accordance with an embodiment of the present invention is made up of biological tissue fabrication information generating device 2 and cell three-dimensional arrangement fabrication device 3.

As shown in FIG. 1 and FIG. 2, biological tissue fabrication information generating device 2 generates biological tissue fabrication information D3 for fabrication of tissue imitative of the structure of biological tissue of a patient Pt from cell(s) based on tissue structure information D1 including information indicating the three-dimensional structure of the biological tissue of said patient Pt obtained when said patient Pt underwent clinical test(s) at a hospital H or other such clinical test facility. In addition, cell three-dimensional arrangement fabrication device 3 fabricates biological tissue T based on biological tissue fabrication information D3 generated by biological tissue fabrication information generating device 2.

The biological tissue T may be employed, for example, for screening to identify drugs appropriate for patient Pt, to conduct a trial graft preliminary to transplantation in patient Pt, or for transplantation in patient Pt, and so forth.

Biological tissue fabrication information generating device 2 is described below. Biological tissue fabrication information generating device 2 may, for example, comprise computer(s). Biological tissue fabrication information generating device 2 may execute prescribed program(s) stored in advance on hard disk drive(s) (HDD), solid state drive(s) (SSD), and/or other such storage device(s), cloud system(s), or the like. As shown in FIG. 3, biological tissue fabrication information generating device 2 may, e.g., by executing such program(s), operate as structure information storage unit(s) 10, biological tissue fabrication information generator(s) 11, cell type information storage unit(s) 12, cell type identification information storage unit(s) 13, cell type information generator(s) 14, substitute cell storage unit(s) 15, support structure information storage unit(s) 16, support structure selector(s) 17, structure difference calculator(s) 18, cell number calculator(s) 19, cell preparation expense information storage unit(s) 20, fabrication expense calculator(s) 21, and output unit(s) 22.

Structure information storage unit 10 stores tissue structure information D1 including three-dimensional structure information indicating the three-dimensional structure of biological tissue obtained when patient Pt underwent clinical test(s) at hospital H or other such clinical test facility. More specifically, structure information storage unit 10 is memory card(s), CD-ROM(s), HDD(s), SSD(s), or other such storage medium or media.

Three-dimensional structure information may be information obtained when patient Pt underwent computerized tomography (x-ray CT) test(s), magnetic resonance imaging (MRI) test(s), positron emission tomography (PET) test(s), ultrasonic test(s), or other such clinical test(s), or information regarding the external dimensions and so forth of patient Pt as photographed using a three-dimensional scanner or the like. Furthermore, tissue structure information D1 may include patient information that does not include three-dimensional structure information such as human leukocyte antigen (HLA) type, allergies, two-dimensional images, and so forth. For example, from the standpoint of the expense of preparing cells and so forth, in a situation where it is necessary to fabricate the biological tissue T from allogeneic cells, cells from a donor having an HLA type such as will permit reduction in the risk of immunological rejection may be selected based on HLA type information for the patient.

Furthermore, while it is possible for such tissue structure information D1 to be only information pertaining to time(s) when disease(s) are contracted by patient Pt, it is also possible to periodically acquire such information during physical checkups or the like and to record this at recording device(s) at hospital(s) H and/or to record this at recording device(s) at data center(s) DC or the like, as shown in FIG. 1 and FIG. 2. Furthermore, tissue structure information D1 may be recorded on recording medium or media by patient Pt himself or herself. Such tissue structure information D1 obtained from past clinical test(s) may be stored at structure information storage unit 10.

Biological tissue fabrication information generator 11 generates biological tissue fabrication information D3 in the form of information linking to respective locations within biological tissue T, and the types of cells that should be arranged at such respective locations, based on tissue structure information D1.

Figure 4:
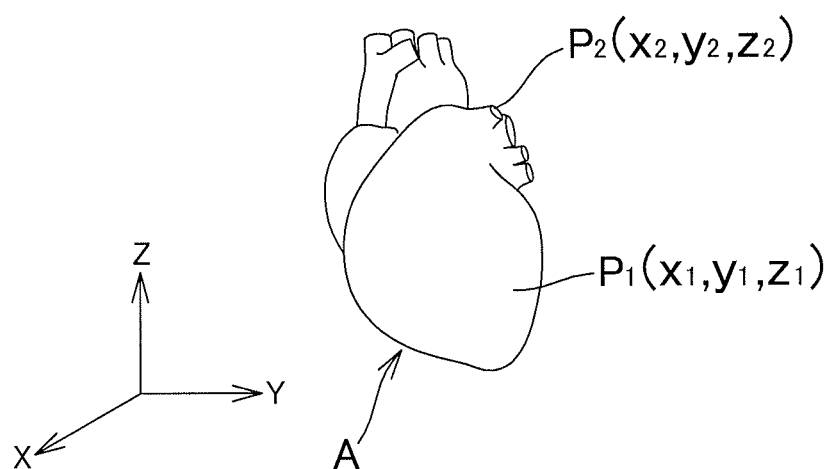
FIG. 4 Drawing for explaining biological tissue fabrication information.

More specifically, biological tissue fabrication information generator 11 analyzes three-dimensional structure based on tissue structure information D1 and displays three-dimensional image(s) A of biological tissue as shown in FIG. 4. In addition, this generates biological tissue fabrication information D3 linking to coordinate points $(x, y, z)$ indicating locations of three-dimensional coordinates in the three-dimensional structure obtained from tissue structure information D1, and the types of cells that should be arranged at such coordinate points.

For example, as shown in FIG. 4, when biological tissue T is the heart, information would be generated such that myocardial cell(s) are arranged at location $P_1$ $(x_1, y_1, z_1)$, and vascular endothelial cell(s) are arranged at location $P_2$ $(x_2, y_2, z_2)$, in a three-dimensional image A of the heart.

As the method by which biological tissue fabrication information generator 11 specifies respective locations within biological tissue T, and types of cells that should be arranged at those respective locations, tissue structure information D1 may be displayed as image(s), and a physician or others such as medical staff or specialist may specify the type(s) of cells for the respective locations based on such image(s).

Furthermore, it is also possible for biological tissue fabrication information generator 11 to, based on three-dimensional structure information included in tissue structure information D1, detect characteristic point(s) in view of the structure of the biological tissue, and to specify type(s) of cells in view of the same. For example, where a structure that bulges in cylindrical fashion at the surface of the heart has been detected, it may be determined that this region is a blood vessel, and it may be specified that the cells of said region are made up of vascular endothelial cells.

Moreover, biological tissue fabrication information generator 11 may specify type(s) of cells based on one or more types of information obtained from any among x-ray CT test(s), MRI test(s), ultrasonic test(s), histologic test(s), flow cytometry, DNA microarray, and/or other such types of clinical tests. For example, types of cells may be specified based on relative magnitude(s) of detected level(s) obtained from any of various types of clinical test data, combination of detected levels obtained from any of various types of clinical test data, or based on cell marker and/or genetic expression information or the like.

Information stored in advance at cell type information storage unit 12 is cell type information D4 indicating types of cells in correspondence to respective locations within each of various reference tissues previously established for use as references for the various types of biological tissue. As an example of information pertaining to the respective locations within the reference tissues, and of types of cells corresponding to those respective locations, information in which types of cells corresponding to respective locations within respective types of biological tissue for each age, sex, body height, and body weight are averaged and linked may be cited.

Biological tissue refers to biological tissue of the heart, liver, kidney, eye, stomach, intestine, skin, bone, or the like. Reference tissue refers to an imaginary model of the structure of standard biological tissue. Separate reference tissue(s) are established for each type of biological tissue.

For example, reference tissue(s) may be established for the heart, reference tissue(s) may be established for the stomach, reference tissue(s) may be established for the intestines, and so forth, a separate reference tissue that models the standard structure of the biological tissue in question being established for each type of biological tissue. In addition, reference tissue information, by means of which reference tissues are expressed in the form of data, may, for example, be stored in advance at cell type information storage unit 12.

Reference tissues are established in correspondence to combinations of pluralities of characteristic conditions that permit characterization of the human body—such as age, sex, body height, and body weight, for example—reference tissues being established in correspondence to combinations of such characteristic conditions. For example, heart reference tissue, stomach reference tissue, intestine reference tissue, and other such respective reference tissues may be established in correspondence to the combination of characteristic conditions "age 30 years, male, body height 170 cm, body weight 60 kg". Respective reference tissues may, for example, be obtained by averaging information pertaining to biological tissue size, shape, and cell types at respective locations within biological tissue, and so forth for persons matching combinations of corresponding characteristic conditions.

Characteristic condition(s) may be established as appropriate. For example, three or less, or five or more kinds of conditions, or one kind of condition may be set; and characteristic condition(s) are not limited to age, sex, body height, and body weight. With respect to respective conditions, e.g., taking the example of age, these may be divided into some ranges such as infant (0 years to 5 years), child (6 years to 15 years), young adult (16 years to 30 years), adult (31 years to 44 years), middle-aged (45 years to 64 years), elderly (65 years or older). With respect to body height and body weight, these may be divided into some ranges similarly. Furthermore, reference tissue(s) are not limited to examples in which these are established in correspondence to combination(s) of plurality or pluralities of characteristic conditions, and reference tissue(s) may be established in correspondence to a single characteristic condition.

Regarding cell type information D4, if biological tissue T to be fabricated is for the heart, information regarding types of cells comprised thereby at respective locations within heart tissue, for each combination of characteristic condition(s), would be stored in advance as cell type information D4. For example, where biological tissue T to be fabricated is for the heart, information indicating that the types of cells constituting respective locations within the left ventricular wall of the heart are "myocardial cells," "fibroblasts," "vascular endothelial cells," and "vascular wall cells"—and cell marker and/or genetic expression information at those myocardial cells, fibroblasts, vascular endothelial cells, and vascular wall cells, and so forth—may be stored in advance as cell type information D4. Further, biological tissue fabrication information generator 11 first selects, from the cell type information D4 stored at cell type information storage unit 12, appropriate cell type information D4 which pertains to reference tissue of the same type as biological tissue T, and then selects therefrom further appropriate cell type information D4, which matches for at least one category of information such as the age, sex, body height, body weight, and so forth of patient Pt. In addition, based on the information thus selected from cell type information D4, biological tissue fabrication information generator 11 links to respective locations within biological tissue T, with the types of cells that should be arranged at those respective locations.

The information stored in advance at cell type identification information storage unit 13 is cell type identification information D5 for identification of cell type(s) based on tissue structure information D1 obtained from biological tissue. More specifically, cell type identification information D5 is information linking to types of cells with relative magnitude(s) of detected level(s) obtained by means of any among x-ray CT test(s), MRI test(s), ultrasonic test(s), histologic test(s), flow cytometry, DNA microarray, and/or other such types of clinical tests, combination of detected levels obtained by means of any of various types of clinical tests, or cell marker and/or genetic expression information.

Cell type information generator 14 generates cell type information D4 based on tissue structure information D1 which includes information permitting identification of cell types at respective locations within the biological tissue of patient Pt and based on cell type identification information D5 stored in advance at cell type identification information storage unit 13.

More specifically, cell type information generator 14 selects cell type identification information D5 for biological tissue of the same type as biological tissue included within tissue structure information D1 based on tissue structure information D1 stored at structure information storage unit 10 and based on cell type identification information D5 stored at cell type identification information storage unit 13. Moreover, by comparing tissue structure information D1 with cell type identification information D5 that has been selected in such fashion, cell type information generator 14 identifies the types of cells at the respective locations in the biological tissue of patient Pt indicated by tissue structure information D1 and generate cell type information D4. For example, cell type information generator 14 may compare cell type identification information D5 with level(s) detected during MRI test(s) and/or x-ray CT test(s) at any desired location(s) obtained from tissue structure information D1 to identify cell type(s) at said location(s) and generate cell type information D4.

The information stored in advance at substitute cell storage unit 15 is substitute cell type information D6 linking to type(s) of cells capable of being substituted for at least some type(s) of cells among the respective types of cells with the type(s) of cells for which they may be substituted. Note that "substitute cell" may refer to a cell provided with functionality equivalent to a cell of the type that was originally intended to be arranged at the biological tissue T being fabricated, and/or may refer to a cell capable of differentiating into a cell of the type that was originally intended to be arranged thereat. In other words, substitute cell storage unit 15 stores information linking to cell type(s) originally intended to be arranged at the biological tissue T being fabricated and cell type(s) capable of being substituted for said cell type(s).

As examples cell types capable of being substituted for cell types originally intended to be arranged thereat, pluripotent stem cells such as induced pluripotent stem cells (iPS cells), embryonic stem cells (ES cells), and multi-lineage differentiating stress enduring (Muse) cells, and endoderm, mesoderm, or ectoderm stem cells/precursor cells (e.g., mesangioblasts, etc.) that can be obtained by inducing differentiation in pluripotent stem cells, adult stem cells such as mesenchymal stem cells, and stem cells into which genes such as will promote differentiation into cells originally intended to be arranged thereat have been introduced, and so forth may be cited. For example, in a situation in which osteoblasts are to be arranged at biological tissue T, besides osteoblasts, it may also be possible to arrange mesenchymal stem cells thereat.

An example of substitute cell type information D6 is shown at FIG. 10. At substitute cell type information D6 shown in FIG. 10, cell types capable of being substituted for cell types originally intended to be arranged thereat are linked to the cell types for which they can be substituted. For example, where the cell type to be arranged thereat is osteoblasts, the corresponding cell types which are capable of being substituted therefor are iPS cells, ES cells, and mesenchymal stem cells. Similarly, where the cell type to be arranged thereat is nerve cells, the corresponding cell types which are capable of being substituted therefor are iPS cells, ES cells, and neural stem cells.

In addition, biological tissue fabrication information generator 11 causes biological tissue fabrication information D3 to be such that substitutable cell type(s) are linked with cell types to be arranged at respective locations based on substitute cell type information D6. Where there are a plurality of substitutable cell types, substitute cell type(s) may be selected consistent with the judgment of a physician or other such medical staff or other such specialist based upon considerations such as the relative difficulty of preparing the respective substitute cell types and so forth.

The information stored in advance at support structure information storage unit 16 is support structure information D8 linking to type(s) of biological tissue T, and type(s) of support structure appropriate for fabrication of said biological tissue T. Linking of said biological tissue T with type(s) of support structure appropriate for fabrication thereof may, for example, be accomplished by causing said biological tissue T to be associated with support structure(s) capable of being used for fabrication thereof. Furthermore, support structure selector 17 selects support structure(s) for use in fabricating said biological tissue T, giving preference to support structure(s) to the extent that they are of satisfactory biocompatibility and of low cost, from support structure information D8 based on biological tissue fabrication information D3, biological tissue fabrication expense information D13, and/or support structure expense and/or the opinion of a physician or other such medical staff or other such specialist with regard to support structure biocompatibility and so forth. In addition, support structure selector 17 generates selected support structure information D9 indicating information regarding the selected support structure(s).

"Support structure" refers to substances for retaining cells within biological tissue, for maintaining the shape and strength of biological tissue, and for inducing improvement in cell function. As support structure, collagen (Types I, II, III, V, and XI), gelatin, elastin, chitosan, fibronectin, vitronectin, laminin, tenascin (TN-C, TN-R, TN-W, TN-X, and TN-Y), alginic acid, hyaluronic acid, recombinant proteins, peptides, and other such substances may be cited as examples. Furthermore, there may be a single support structure constituent, or there may be two or more thereof. Moreover, different support structures may be employed in different zones within the biological tissue.

More specifically, where biological tissue T to be fabricated is myocardial tissue, information pertaining to collagen, fibronectin, laminin, artificial matrices, and so forth— these being among the aforementioned support structures— is stored as support structure information D8. Support structure selector 17 selects support structure(s) to be used from among these support structures. Biological tissue fabrication information generator 11 generates biological tissue fabrication information D3 such as will cause the support structure(s) selected by support structure selector 17 to be employed for fabrication of biological tissue T.

Based on tissue structure information D1 for patient Pt and tissue structure information D1 which is an earlier version thereof than that tissue structure information D1 for that patient Pt, structure difference calculator 18 determines the difference between the structure indicated by the tissue structure information D1 and the structure indicated by the earlier version of that tissue structure information D1. More specifically, where patient Pt has previously undergone clinical testing yearly or once every several years, each time that patient Pt undergoes clinical test(s), tissue structure information D1 obtained as a result of the clinical test(s) is stored in cumulative fashion at data center DC or the like. When patient Pt is diseased or injured or in some other such state as to require fabrication of biological tissue T, structure difference calculator 18 compares three-dimensional structure information included within a current version of tissue structure information D1 for said patient Pt, and three-dimensional structure information included within the most recent healthy version of tissue structure information D1, to detect structural difference(s) therebetween. In addition, structure difference calculator 18 causes structure difference information D10 to be generated that comprises the most recent, i.e., an earlier version of, tissue structure information D1 for portion(s) where structural difference(s) have been detected. In addition, based on structure difference information D10, biological tissue fabrication information generator 11 generates biological tissue fabrication information D3 indicating the structure of biological tissue T.

Figure 5:
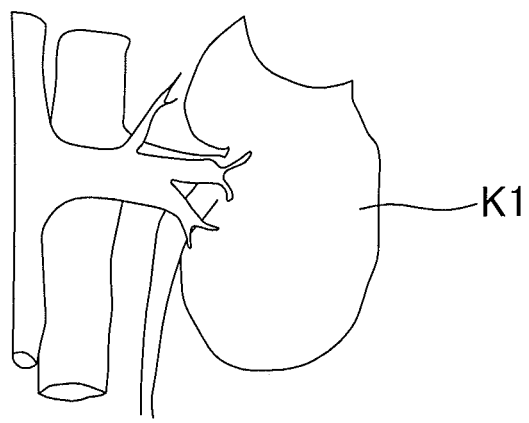
FIG. 5($a$) is a three-dimensional image of a kidney indicated by a current version of tissue structure information for a situation in which a portion of the kidney has been removed due to renal cancer.
Figure 5:
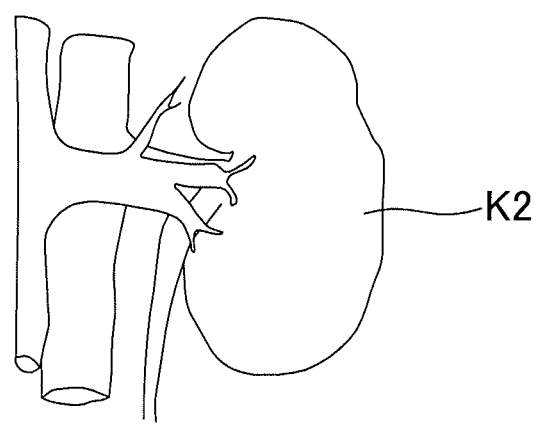
Figure 5:

FIG. 5(a) is an explanatory diagram showing a three-dimensional image of kidney K1 indicated by a current version of tissue structure information D1 for patient Pt who has had a portion of his or her kidney removed due to renal cancer; FIG. 5(b) is an explanatory diagram showing a three-dimensional image of kidney K2 indicated by the most recent healthy version of tissue structure information D1 prior to partial nephrectomy; and FIG. 5(c) is an explanatory diagram showing a three-dimensional image of kidney K3 at the portion of the three-dimensional structure indicated by structure difference information D10. Next, structure difference calculator 18 will be described in terms of an example with reference to FIG. 5. For example, in a situation in which a portion of the kidney is currently missing as shown in FIG. 5(a), structure difference calculator 18 obtains the most recent healthy version of tissue structure information D1 shown at FIG. 5(b) and the current tissue structure information D1 shown at FIG. 5(a). In addition, structure difference calculator 18 detects structural difference(s) between the current version of tissue structure information D1 and the most recent, i.e., earlier version of, tissue structure information D1, and extracts the most recent version of tissue structure information D1 for region(s) where structural difference(s) have been detected as shown at FIG. 5(c) to generate structure difference information D10. In addition, biological tissue fabrication information generator 11 generates biological tissue fabrication information D3 indicating the structure of the biological tissue T to be fabricated which is information indicating the three-dimensional structure of the portion indicated at structure difference information D10 before that portion came to be missing.

Thus, it is possible to compare information pertaining to biological tissue obtained in the past when patient Pt underwent clinical test(s) to information pertaining to said biological tissue in the present, determine structural difference(s) therebetween, and fabricate biological tissue T corresponding to differing portion(s), i.e., the portion(s) indicated at FIG. 5(c). Note that although the foregoing was described in terms of an example in which the kidney was employed as biological tissue T, the biological tissue is not limited to that of the kidney. Moreover, this may be employed for fabrication of biological tissue for which the external shape of the tissue is aesthetically important, such as is the case with regions targeted for aesthetic plastic surgery. For example, in a situation in which a breast has been completely removed due to breast cancer, biological tissue fabrication information D3 for breast tissue identical in structure to the breast that was removed may be generated from tissue structure information D1 from data from x-ray CT test(s) or other such clinical test(s) or from image data produced by using a three-dimensional scanner or the like to scan the healthy breast prior to removal thereof.

Cell number calculator 19 calculates the number of cells required for fabrication of biological tissue T based on the biological tissue fabrication information D3 generated by biological tissue fabrication information generator 11. In addition, cell number information D11 indicating the number of cells determined as a result of calculation is used by culture apparatus 4 and/or fabrication expense calculator 21, described below.

More specifically, information pertaining to types of biological tissue, and to average cell density of each zone within the respective biological tissues, is stored in advance. In addition, by determining the volume of each zone within the biological tissue(s) T to be fabricated, the number of cells required for fabrication of biological tissue(s) T may be calculated from biological tissue fabrication information D3 based on information pertaining to the volumes of each of those zones and average cell density at each zone within the aforementioned respective biological tissue(s). While it is possible to calculate the total number of all cells required for fabrication of biological tissue(s) T, it is preferred that calculation of cell number be such that the number of cells is calculated separately for each cell type.

The information stored in advance at cell preparation expense information storage unit 20 is cell preparation expense information D12 linking to number(s) of cells, and information pertaining to the expense of preparing such number(s) of cells. While cell preparation expense information D12 may link to expense information as a function of cell number without regard to cell type, so as to permit more accurate calculation of expense it is preferred that information pertaining to the expense of preparing cells as a function of cell number be linked thereto separately for different cell types. Furthermore, cell preparation expense information D12 may include information pertaining to expense of procuring support structures and/or cells employed for fabrication of biological tissue(s) T, expense of shipping fabricated biological tissue(s) T, and so forth.

Based on number(s) of cells calculated by cell number calculator 19 and cell preparation expense information D12 stored at cell preparation expense information storage unit 20, fabrication expense calculator 21 calculates biological tissue fabrication expense information D13 for fabrication of biological tissue(s) T. Where cell preparation expense information D12 is stored separately depending on cell types at cell preparation expense information storage unit 20, it is preferred that fabrication expense calculator 21 cause biological tissue fabrication expense for biological tissue(s) T to be calculated based on cell preparation expense that is calculated separately for different cell types.

Output unit 22 causes information from biological tissue fabrication information generator 11, cell number calculator 19, and fabrication expense calculator 21 to be output to cell three-dimensional arrangement fabrication device 3, and/or culture apparatus 4, or to another computer or other such equipment, as described below. For example, output unit 22 may cause biological tissue fabrication information D3 generated at biological tissue fabrication information generator 11 to be output to cell three-dimensional arrangement fabrication device 3, and may cause cell number information D11 generated by cell number calculator 19 and biological tissue fabrication information D3 to be output to culture apparatus 4. Furthermore, at medical expense calculation system 5A and medical expense calculation system 5B, output unit 22 causes biological tissue fabrication information D3 generated by biological tissue fabrication information generator 11 and/or biological tissue fabrication expense information D13 generated by fabrication expense calculator 21 to be output to treatment expense calculation device 6A, treatment expense calculation device 6B, and medical expense calculation device 7, described below.

Cell three-dimensional arrangement fabrication device 3 is provided with cell three-dimensional arrangement unit 30 which fabricates biological tissue T by causing separately prepared cells to be three-dimensionally arranged based on biological tissue fabrication information D3 generated by biological tissue fabrication information generating device 2. While there is no particular limitation with respect to the method by which cell three-dimensional arrangement unit 30 is employed to cause cells to be three-dimensionally arranged, cells may be arranged one cell at a time, or arrangement may proceed through placement of previously prepared clusters of cell aggregates and/or cells prepared using culture apparatus 4, described below, or the like.

As the foregoing method by which cells are three-dimensionally arranged, the dispensing technique, inkjet technique, laser-mediated cell transfer technique, and so forth may be cited as examples. The foregoing dispensing technique is a procedure in which ink material placed in a syringe is shaped as a result of being extruded from the nozzle portion thereof in continuous fashion by means of a pneumatic or mechanical driven apparatus, permitting expulsion of highly viscous solutions and/or solutions containing clusters of cell aggregates. The foregoing inkjet technique is a procedure in which shaping is carried out by causing individual cells to be propelled by piezoelectric, thermal, electric field, or other such means, permitting propulsion from multiple nozzles and high-resolution rendering. The foregoing laser-mediated cell transfer technique is a procedure in which cells are applied to a glass substrate having a light-absorbing layer, use of a pulsed laser beam, the light from which is collected onto a single spot, to irradiate the light-absorbing layer from the back side thereof causing shaping to proceed as a result of propulsion of the cells that were applied to the glass plate, permitting expulsion of highly viscous solutions in such fashion that the very concept of clogged nozzles is irrelevant.

Furthermore, cell three-dimensional arrangement fabrication device 3 may be provided with functionality such as will cause culturing to take place after cells have been three-dimensionally arranged. In particular, where ES cells or iPS cells are employed as substitute cell type(s) for cell type(s) originally intended to be arranged at biological tissue T, because there would be a risk of tumor formation if such cells were transplanted in their undifferentiated state, culturing for induction of differentiation following arrangement of the ES cells or iPS cells is essential. Furthermore, where adult stem cells and/or precursor cells are employed as substitute cell type(s), following arrangement of such cells, culturing for induction of differentiation into cell type(s)

originally intended to be arranged thereat should be carried out. As cell three-dimensional arrangement fabrication device 3, a Regenova 3D Bioprinter manufactured by Cyfuse Biomedical K.K. may, for example, be employed.

As shown in FIG. 1, FIG. 2, and FIG. 3, biological tissue fabrication system 1B in accordance with an embodiment of the present invention is made up of biological tissue fabrication information generating device 2, cell three-dimensional arrangement fabrication device 3, and culture apparatus 4.

Culture apparatus 4 will now be described. Culture apparatus 4, which is an apparatus for preparing cells, is capable of determining culture conditions suitable for carrying out culture in correspondence to cell type. Moreover, it may have functionality permitting promotion of differentiation and/or growth of cells. Furthermore, it may be provided with high-efficiency particulate air filter(s) (HEPA filter(s)) and/or other such filter(s) for carrying out purification of air so as to prevent contamination by saprophytic organisms and so forth when air from the exterior is drawn into the culture space. As culture apparatus 4, a P4CS Automatic Closed Cell Culture Device manufactured by Kaneka Corporation may, for example, be employed.

Culture apparatus 4 is provided with culture conditions determining unit 40 which determines culture conditions for cells of the respective types required for fabrication of biological tissue based on biological tissue fabrication information D3. Culture conditions determining unit 40 determines culture conditions for achieving the number of cells required for fabrication of biological tissue T by generating cells of the respective type(s) based on cell number information D11 for the number of cells required for fabrication of biological tissue T as calculated by cell number calculator 19, and/or the number of cells that would be determined to be necessary for fabrication of biological tissue T by one of skill in the art, and information pertaining to cell type(s) obtainable from biological tissue fabrication information D3.

The information stored in advance at culture conditions determining unit 40 is temperature, medium, medium replacement frequency, culture time, and/or other such information pertaining to culture conditions suitable for respective cell type(s). Furthermore, oxygen concentration, pH conditions, carbon dioxide concentration, substance(s) to be added to medium, and/or other such information pertaining to culture conditions suitable for respective cell type(s) may be stored thereat. Culture conditions determining unit 40 determines culture conditions such as will accommodate the type(s) of cells and the number(s) of cells. For example, lookup table(s) linking to culture conditions with numbers of cells and types of cells to be cultured may be stored in advance, and culture conditions may be determined by referring to such lookup table(s).

Figure 6:
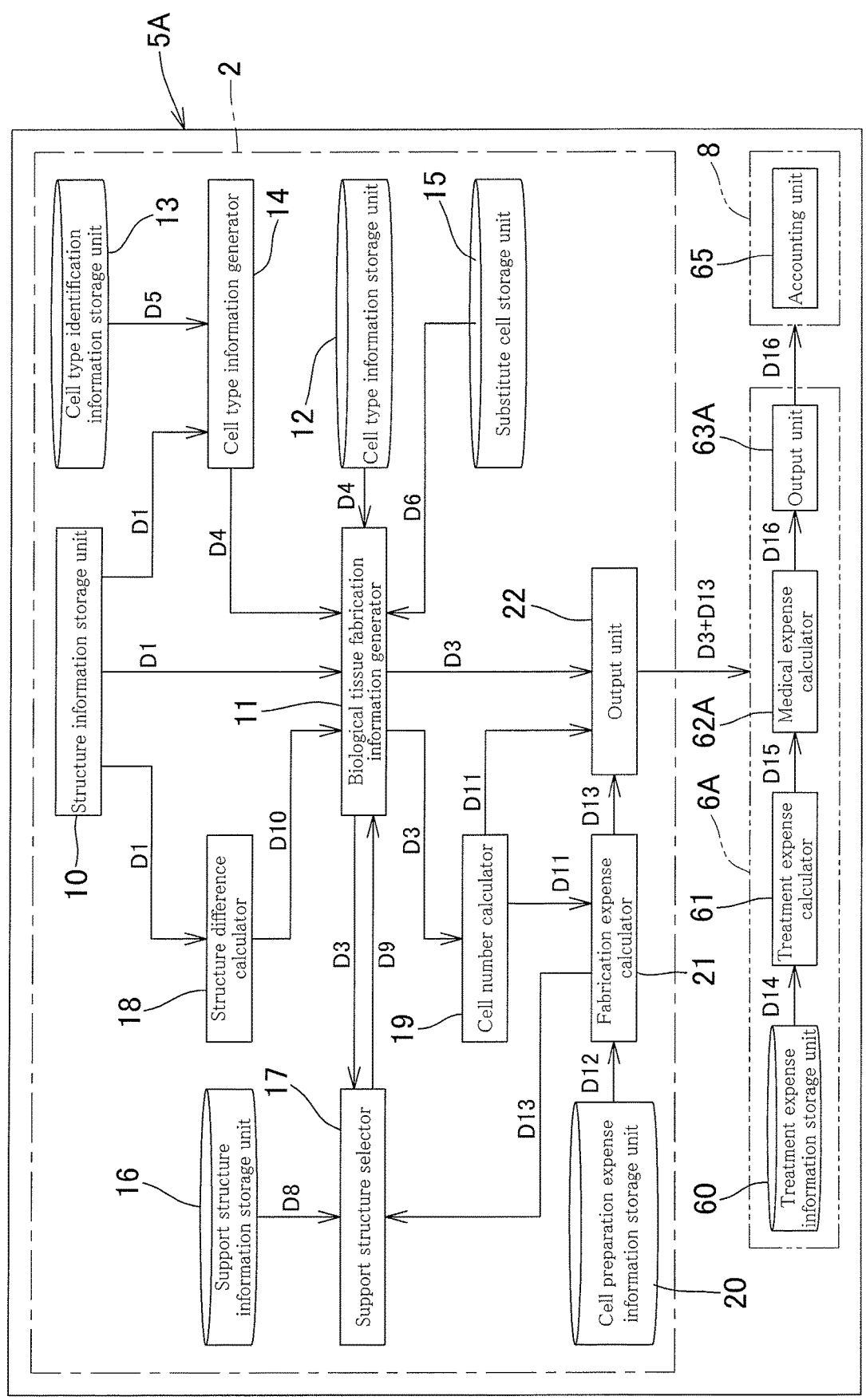
FIG. 6 Block diagram showing exemplary constitution of a medical expense calculation system and the biological tissue fabrication information generating device shown in FIG. 1.

As shown in FIG. 6, medical expense calculation system 5A in accordance with an embodiment of the present invention comprises biological tissue fabrication information generating device 2, treatment expense calculation device 6A having treatment expense calculator 61 and medical expense calculator 62A, and accounting device 8. Note that it is not necessary for medical expense calculation system 5A to contain accounting device 8.

As biological tissue fabrication information generating device 2 has already been described, description here will be omitted.

Treatment expense calculation device 6A may, for example, comprise computer(s) and/or the like. Treatment expense calculation device 6A is capable of executing prescribed program(s) stored in advance on hard disk drive(s) (HDD), solid state drive(s) (SSD), and/or other such storage device(s), cloud system(s), or the like. By executing said program(s), treatment expense calculation device 6A functions as treatment expense information storage unit(s) 60, treatment expense calculator(s) 61, medical expense calculator(s) 62A, and output unit(s) 63A such as are shown in FIG. 6.

The information stored in advance at treatment expense information storage unit 60 is treatment expense information D14 pertaining to expense of treatment employing grafting of biological tissue. Treatment expense information D14 is information linking to expense of medical examination, surgery, and hospital admission for respective type(s) of biological tissue(s) T to be grafted. Furthermore, expense may be further linked to respective types of biological tissue T to be grafted, it may also be linked separately and in detailed fashion for respective locations, sizes, and so forth of biological tissue T.

Treatment expense calculator 61 calculates expense of treatment for a patient receiving graft(s) of biological tissue T. More specifically, treatment expense calculator 61 calculates treatment expense information D15 based on biological tissue fabrication information D3 generated at biological tissue fabrication information generating device 2 and treatment expense information D14 stored at treatment expense information storage unit 60. Note that treatment expense calculator 61 need not necessarily carry out calculation based on biological tissue fabrication information D3, and it is possible for treatment expense information D15 to be calculated based on treatment expense information D14 and information pertaining to type(s), size(s), location(s), and so forth of biological tissue(s) T as manually entered at treatment expense calculation device 6A by a physician or other such medical staff.

Medical expense calculator 62A calculates medical expense information D16 for a patient receiving therapeutic graft(s) of biological tissue T based on treatment expense information D15 calculated by treatment expense calculator 61 and biological tissue fabrication expense information D13 calculated by fabrication expense calculator 21 of biological tissue fabrication information generating device 2.

Output unit 63A of treatment expense calculation device 6A in accordance with the present embodiment causes medical expense information D16 calculated by medical expense calculator 62A to be output to accounting device 8.

Accounting device 8 is a device for managing medical expense(s) of patient(s). More specifically, accounting unit 65 of accounting device 8 receives medical expense information D16 to manage medical expense. Accounting device 8 may, for example, be installed in the administration department or the like of a medical institution so as to permit medical staff to ascertain medical expense. This will make it possible for medical staff to present quotation(s) for medical expense to a patient receiving therapeutic graft(s) of biological tissue T.

Figure 7:
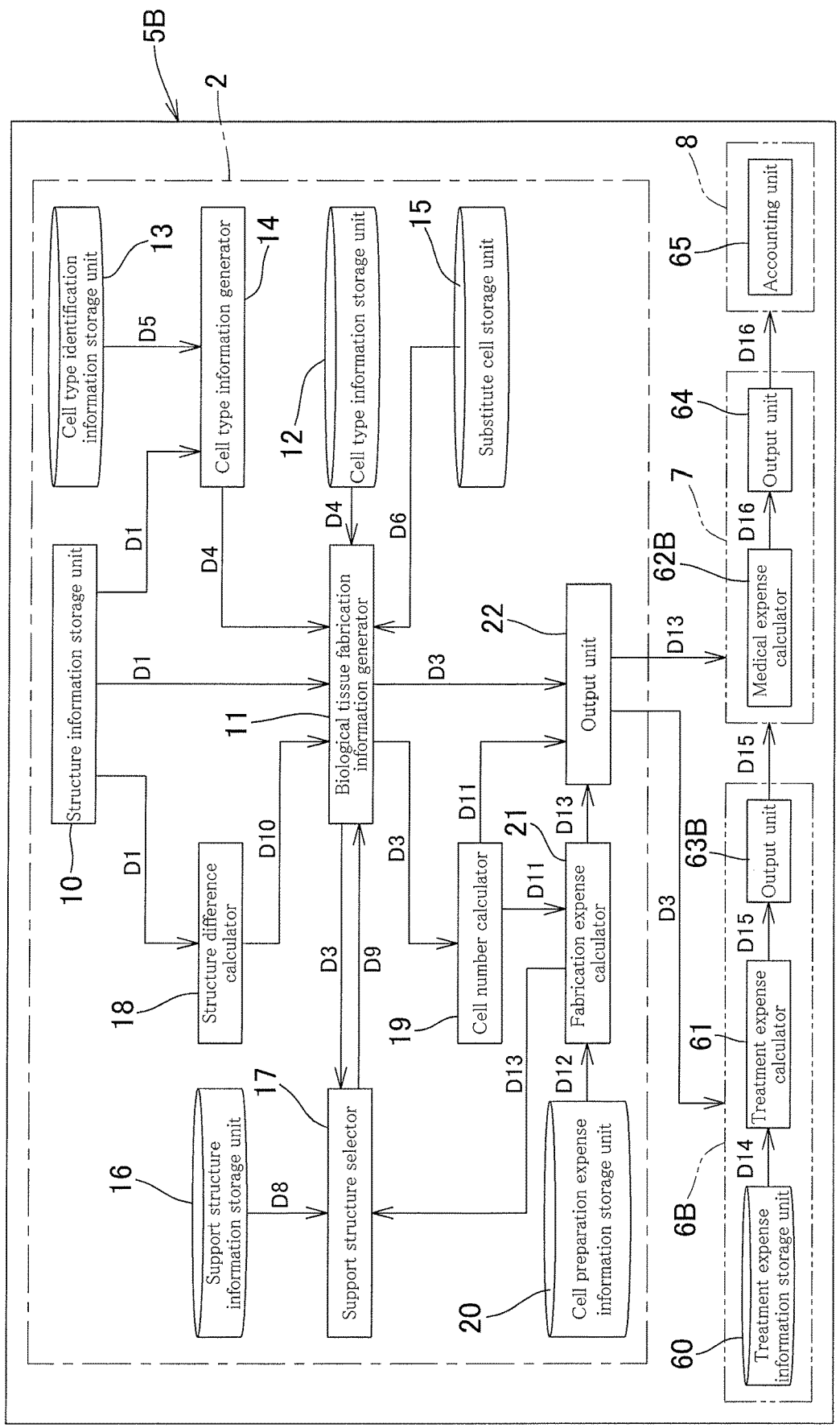
FIG. 7 Block diagram showing exemplary constitution of a medical expense calculation system and the biological tissue fabrication information generating device shown in FIG. 2 in the context of an example that is different from that shown in FIG. 6.

As shown in FIG. 7, medical expense calculation system 5B in accordance with an embodiment of the present invention is made up of biological tissue fabrication information generating device 2, treatment expense calculation device 6B having treatment expense calculator 61, and medical expense calculation device 7 having medical expense calculator 62B.

As biological tissue fabrication information generating device 2 has already been described, description here will be omitted.

Treatment expense calculation device 6B may, for example, comprise computer(s) and/or the like. Treatment expense calculation device 6B is capable of executing prescribed program(s) stored in advance on hard disk drive(s) (HDD), solid state drive(s) (SSD), and/or other such storage device(s), cloud system(s), or the like. In addition, treatment expense calculation device 6B functions as treatment expense information storage unit(s) 60, treatment expense calculator(s) 61, and output unit(s) 63B such as are shown in FIG. 7.

Treatment expense calculator 61 calculates expense of treatment for a patient receiving graft(s) of biological tissue T. More specifically, treatment expense calculator 61 calculates treatment expense information D15 based on biological tissue fabrication information D3 generated at biological tissue fabrication information generating device 2 and treatment expense information D14 stored at treatment expense information storage unit 60. Note that treatment expense calculator 61 need not necessarily carry out calculation based on biological tissue fabrication information D3, and it is possible for treatment expense information D15 to be calculated based on treatment expense information D14 and information pertaining to type(s), size(s), location(s), and so forth of biological tissue(s) T as manually entered at treatment expense calculation device 6B by a physician or other such medical staff.

Output unit 63B causes treatment expense information D15 calculated by treatment expense calculator 61 to be output to medical expense calculation device 7.

Medical expense calculator 62B of medical expense calculation device 7 calculates medical expense information D16 for a patient receiving therapeutic graft(s) of biological tissue T based on treatment expense information D15 calculated by treatment expense calculation device 6B and biological tissue fabrication expense information D13 calculated by fabrication expense calculator 21 of biological tissue fabrication information generating device 2.

Output unit 64 causes medical expense information D16 generated by medical expense calculator 62B to be output to accounting device 8.

As accounting device 8 has already been described, description here will be omitted.

Furthermore, a medical expense calculation system in accordance with an embodiment of the present invention may be provided with biological tissue fabrication information generating device 2 and treatment expense calculation device 6B having treatment expense calculator 61 are shown in FIG. 7, but need not be provided with medical expense calculation device 7. That is, medical expense may be calculated manually by medical staff or the like based on biological tissue fabrication expense information D13 generated by biological tissue fabrication information generating device 2 and treatment expense information D15 generated by treatment expense calculation device 6B.

Figure 8:
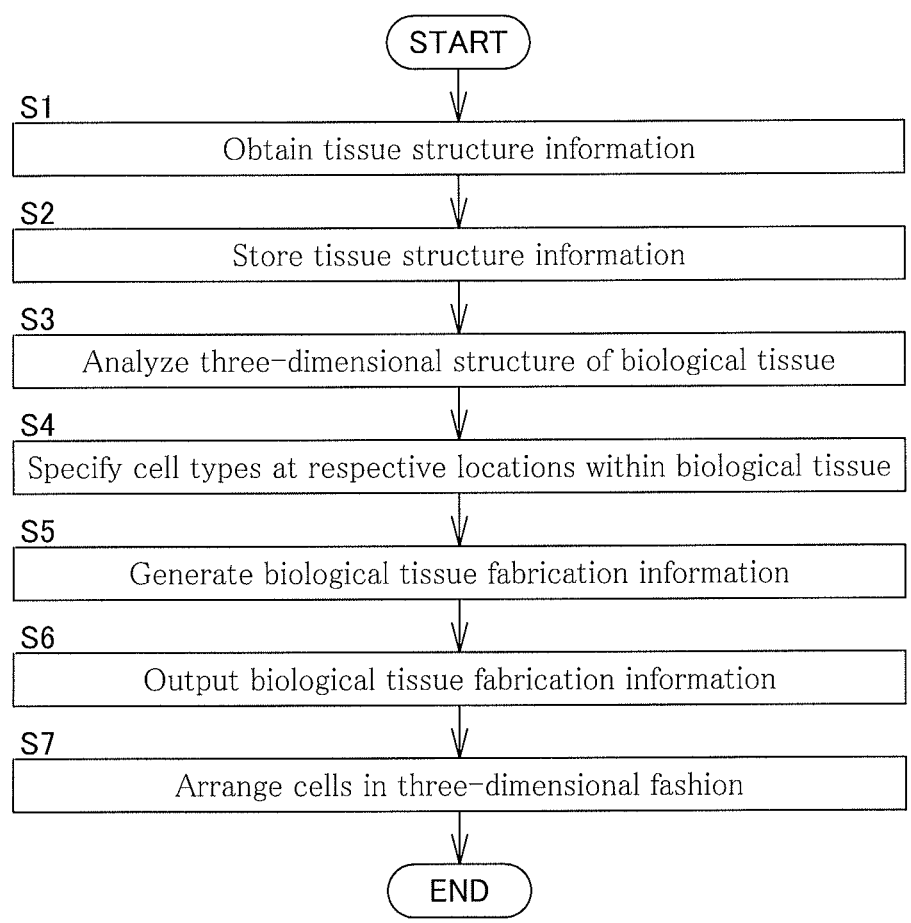
FIG. 8 Exemplary flowchart pertaining to a biological tissue fabrication information generating device and a biological tissue fabrication system.

FIG. 8 is an example of a flowchart pertaining to biological tissue fabrication information generating device 2, biological tissue fabrication system 1A, and biological tissue fabrication system 1B. Referring to FIG. 1, FIG. 2, FIG. 3, and FIG. 8, biological tissue fabrication information generating device 2, biological tissue fabrication system 1A, and biological tissue fabrication system 1B will now be described.

Patient Pt undergoes an x-ray CT test or other clinical tests at hospital H or other clinical test facility, whereby tissue structure information D1 is obtained (step S1). This tissue structure information D1 is stored at structure information storage unit 10 (step S2). Where past tissue structure information D1 of said patient Pt is stored at hospital H, data center DC, and/or the like, past tissue structure information D1 may also be stored at structure information storage unit 10.

Next, biological tissue fabrication information generator 11 analyzes the three-dimensional structure of the biological tissue based on tissue structure information D1 (step S3). If past tissue structure information D1 of said patient is available, structure difference calculator 18 may detect difference(s) between the structures of past and present biological tissue.

Next, based on tissue structure information D1, biological tissue fabrication information generator 11 specifies type(s) of cells that should be arranged at respective locations within biological tissue(s) T (step S4). Furthermore, based on substitute cell type information D6 stored in advance at substitute cell storage unit 15, biological tissue fabrication information generator 11 may select cell type(s) capable of being substituted for cell type(s) originally intended to be arranged at biological tissue(s) T. Moreover, support structure selector 17 may select support structure(s) for use in fabricating said biological tissue T from support structure information D8 based on biological tissue fabrication information D3, biological tissue fabrication expense information D13, and/or support structure expense and/or the opinion of a physician or other such medical staff or other such specialist regarding support structure biocompatibility and so forth.

Biological tissue fabrication information generator 11 generates biological tissue fabrication information D3 in the form of type(s) of cells to be arranged at respective locations within biological tissue(s) T as indicated at tissue structure information D1 (step S5). Furthermore, cell number calculator 19 may calculate the number of cells required for fabrication of biological tissue(s) T based on biological tissue fabrication information D3. Moreover, based on number(s) of cells calculated at cell number calculator 19 and cell preparation expense information D12 stored in advance at cell preparation expense information storage unit 20, fabrication expense calculator 21 may calculate the expense of fabricating biological tissue(s) T.

Biological tissue fabrication information generating device 2 causes biological tissue fabrication information D3 to be output to cell three-dimensional arrangement fabrication device 3 (step S6). Furthermore, biological tissue fabrication information D3 may be output to culture apparatus 4. Moreover, if cell number calculator 19 is to calculate the number of cells required for fabrication of biological tissue(s) T, cell number information D11, which is information pertaining to the required number of cells, may be output to culture apparatus 4 together with biological tissue fabrication information D3. If information is output to culture apparatus 4, culture conditions determining unit 40 determines culture conditions for cells of respective type(s) required for fabrication of biological tissue(s) T based on that information, and culture apparatus 4 prepares cells of the respective type(s).

Based on biological tissue fabrication information D3, cell three-dimensional arrangement unit 30 of cell three-dimensional arrangement fabrication device 3 fabricates biological tissue(s) T by causing cells to be three-dimensionally arranged (step S7).

Because biological tissue fabrication information generating device 2 constituted as described above generates information linking to respective locations within biological tissue T at which fabrication is to be carried out and type(s) of cells that should be arranged at those respective locations based on information pertaining to the three-dimensional structure of biological tissue obtainable from a patient, biological tissue fabrication system 1A and biological tissue fabrication system 1B are able, based on this information, to precisely fabricate biological tissue imitative of the structure of the biological tissue of a patient comprising cells of a plurality of types that are systematically arranged in sophisticated fashion.

Although biological tissue fabrication information generating device 2, biological tissue fabrication system 1A, and biological tissue fabrication system 1B at the foregoing working examples had as object the fabrication of biological tissue T to be grafted in patient Pt, these may also be employed to fabricate biological tissue T that is in a deteriorated state due to disease or the like, or biological tissue T that is identical to tissue to be grafted for the purpose of conducting trial graft(s). Because this will permit trial graft(s) to be conducted, this will make it possible to improve the success rate of difficult surgical procedures. In addition, biological tissue T may be employed for screening of drug(s) for patient Pt, making it possible to perform screening to determine the suitability of drug(s) for the patient.

Figure 9:
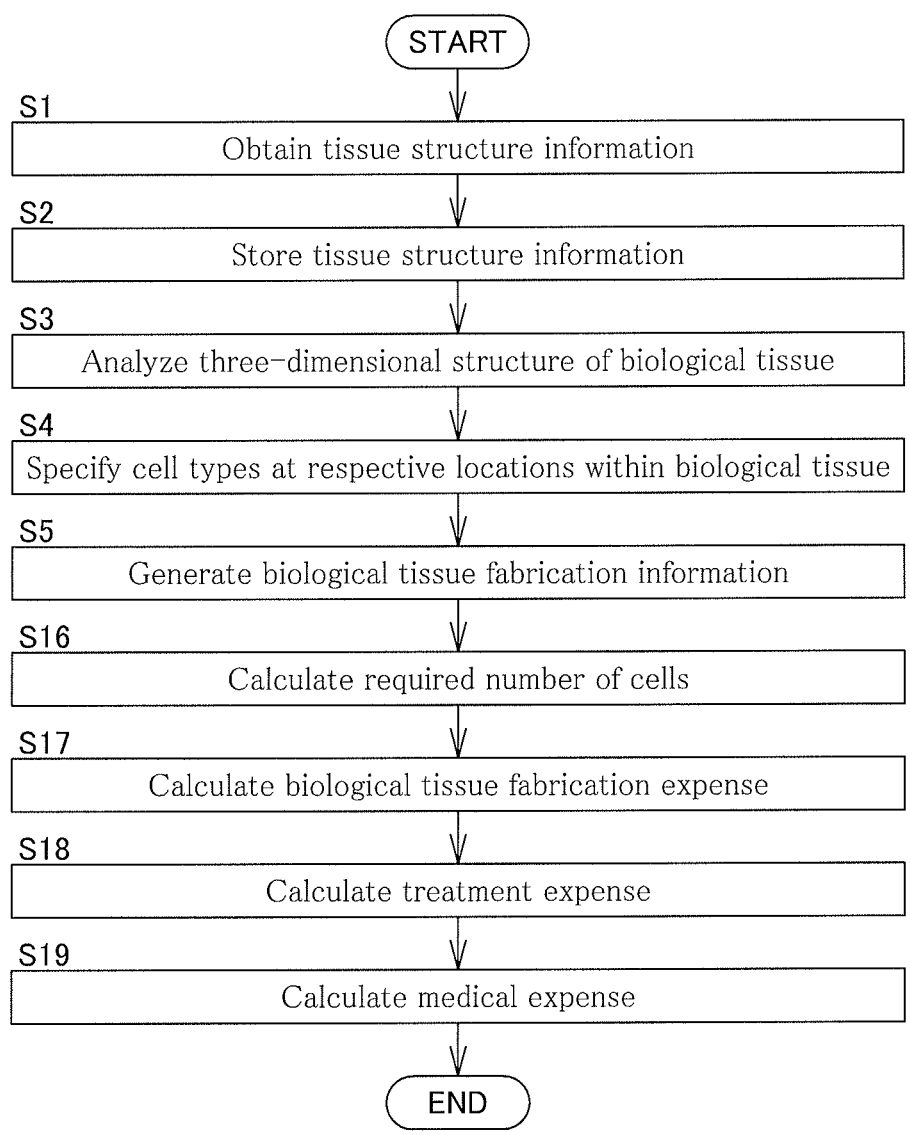
FIG. 9 Exemplary flowchart pertaining to a biological tissue fabrication information generating device and a medical expense calculation system.

FIG. 9 is an example of a flowchart pertaining to biological tissue fabrication information generating device 2, medical expense calculation system 5A, and medical expense calculation system 5B. Referring to FIG. 1, FIG. 2, FIG. 6, FIG. 7, and FIG. 9, biological tissue fabrication information generating device 2, medical expense calculation system 5A, and medical expense calculation system 5B will now be described.

Step S1 to step S5 at FIG. 9 being similar to step S1 to step S5 at FIG. 8, as these have already been described, description thereof will be omitted here.

Cell number calculator 19 of biological tissue fabrication information generating device 2 calculates the number of cells required for fabrication of biological tissue(s) T based on biological tissue fabrication information D3, and generates cell number information D11 (step S16). In addition, based on cell preparation expense information D12 stored in advance at cell preparation expense information storage unit 20 and cell number information D11, fabrication expense calculator 21 of biological tissue fabrication information generating device 2 calculates the expense of fabricating biological tissue(s) T (step S17).

Next, treatment expense calculation device 6B or treatment expense calculator 61 of treatment expense calculation device 6A calculates treatment expense based on treatment expense information D14 stored at treatment expense information storage unit 60 and biological tissue fabrication information D3 generated by biological tissue fabrication information generating device 2 (step S18). Note that treatment expense calculation device 6B or treatment expense calculator 61 of treatment expense calculation device 6A need not necessarily carry out calculation based on biological tissue fabrication information D3, and it is possible for treatment expense to be calculated based on treatment expense information D14 and information pertaining to type(s), size(s), location(s), and so forth of biological tissue(s) T as entered at treatment expense calculation device 6A or treatment expense calculation device 6B by a physician or other such medical staff.

Based on biological tissue fabrication expense information D13 calculated at cell number calculator 19 of biological tissue fabrication information generating device 2 and treatment expense information D15 calculated by treatment expense calculation device 6B or treatment expense calculator 61 of treatment expense calculation device 6A, medical expense calculation device 7 or medical expense calculator 62A of treatment expense calculation device 6A calculates medical expense for the patient receiving graft(s) of biological tissue(s) T (step S19).

Medical expense calculation system 5A and medical expense calculation system 5B constituted as described above are configured such that biological tissue fabrication information generating device 2 calculates the expense of fabricating biological tissue(s) T, and treatment expense calculation device 6A or treatment expense calculation device 6B calculates the expense of treatment for a patient Pt receiving therapeutic graft(s) of biological tissue(s) T. In addition, treatment expense calculation device 6A or medical expense calculation device 7 may calculate medical expense for patient Pt based on the expense of fabricating biological tissue(s) T and the expense of treatment for patient Pt.

EXPLANATION OF REFERENCE NUMERALS

1A Biological tissue fabrication system
1B Biological tissue fabrication system
2 Biological tissue fabrication information generating device
3 Cell three-dimensional arrangement fabrication device
4 Culture apparatus
5A Medical expense calculation system
5B Medical expense calculation system
6A Treatment expense calculation device
6B Treatment expense calculation device
7 Medical expense calculation device
8 Accounting device
10 Structure information storage unit
11 Biological tissue fabrication information generator
12 Cell type information storage unit
13 Cell type identification information storage unit
14 Cell type information generator
15 Substitute cell storage unit
16 Support structure information storage unit
17 Support structure selector
18 Structure difference calculator
19 Cell number calculator
20 Cell preparation expense information storage unit
21 Fabrication expense calculator
22 Output unit
30 Cell three-dimensional arrangement unit
40 Culture conditions determining unit
60 Treatment expense information storage unit
61 Treatment expense calculator
62A Medical expense calculator
62B Medical expense calculator
63A Output unit
63B Output unit
64 Output unit
65 Accounting unit
D1 Tissue structure information
D3 Biological tissue fabrication information
D4 Cell type information
D5 Cell type identification information
D6 Substitute cell type information
D8 Support structure information
D9 Selected support structure information
D10 Structure difference information
D11 Cell number information
D12 Cell preparation expense information
D13 Biological tissue fabrication expense information D14 Graft treatment expense information
D15 Treatment expense information
D16 Medical expense information
DC Data center
H Hospital
K Kidney
P Location
Pt Patient
T Biological tissue

The invention claimed is:

1. A biological tissue fabrication information generating device that generates biological tissue fabrication information for the fabrication of a biological tissue of a patient from cells, the biological tissue fabrication information generating device comprising:
   a structure information storage unit that stores tissue structure information indicating a three-dimensional structure of the biological tissue of the patient;
   a cell type information storage unit which stores a cell type information for determining cell types at respective locations in the biological tissue indicated by the tissue structure information, wherein the cell type information is stored in advance;
   a biological tissue fabrication information generator that, based on the tissue structure information and the cell type information, generates the biological tissue fabrication information in which the respective locations in the biological tissue are linked to the cell types to be arranged at the respective locations;
   a cell number calculator that calculates a number of cells required for fabrication of the biological tissue based on the biological tissue fabrication information generated by the biological tissue fabrication information generator;
   a cell preparation expense information storage unit which stores cell preparation expense information linking a number of cells and information pertaining to an expense of preparing that number of cells; and
   a fabrication expense calculator that, based on the cell preparation expense information and the number of cells required for fabrication of the biological tissue calculated by the cell number calculator, calculates biological tissue fabrication expense for fabrication of the biological tissue, so that the biological tissue fabrication information generating device generates biological tissue fabrication expense information.

2. A medical expense calculation system for calculating a medical expense of a patient receiving a therapeutic graft formed of a biological tissue, the medical expense calculation system comprising:
   the biological tissue fabrication information generating device according to claim 1; and
   a treatment expense calculation device comprising a treatment expense calculator for calculating a treatment expense required for a therapeutic graft formed of the biological tissue and generating a treatment expense information,
   wherein the biological tissue fabrication information generating device and the treatment expense calculation device are configured to calculate a total medical expense of the patient receiving the therapeutic graft formed of the biological tissue based on the biological tissue fabrication expense information generated by the biological tissue fabrication information generating device and the treatment expense information generated by the treatment expense calculator, the total medical expense including both the treatment expense and the biological tissue fabrication expense.

* * * * *